United States Patent
Arnold et al.

(10) Patent No.: US 6,347,239 B1
(45) Date of Patent: Feb. 12, 2002

(54) METHOD OF EVALUATING THE EFFICACY OF DRUG ON BRAIN NERVE CELLS

(76) Inventors: Douglas L. Arnold, 3605 University Street #5, Montréal, Québec (CA), H3A 2B3; Neil Cashman, 3859 Draper Avenue, Montréal, Québec (CA), H4A 2N9; Sanjay Kalra, 1563 Docteur Penfield #2, Montréal, Québec (CA), H3G 1C6

( * ) Notice: Subject to any disclaimer, the term of this patent is extended or adjusted under 35 U.S.C. 154(b) by 0 days.

(21) Appl. No.: 09/180,776
(22) PCT Filed: Mar. 13, 1998
(86) PCT No.: PCT/CA98/00230
  § 371 Date: Nov. 13, 1998
  § 102(e) Date: Nov. 13, 1998
(87) PCT Pub. No.: WO98/41882
  PCT Pub. Date: Sep. 24, 1998

(51) Int. Cl.$^7$ .............................................. A61B 5/055
(52) U.S. Cl. ........................ 600/410; 324/307; 324/309
(58) Field of Search ................................ 600/410, 309; 324/307, 309; 436/173

(56) References Cited

U.S. PATENT DOCUMENTS 5,617,861 A * 4/1997 Ross et al.
5,889,033 A * 3/1999 Kaminski .................... 514/370
6,133,306 A * 10/2000 Beal ........................... 514/418

OTHER PUBLICATIONS

De Stefano et al. "Reversible Decreases in N–Acetylaspartate after Acute" Mag. Reson. Med. 721–727, Jun. 1995.*

Arnold, "Reversible Reduction of N–acetylaspartate after Acute Central Nervous" Mag. Reson. Med., 643, 1993.*

De Stefano et al. "Correlation Between brain lesion load on MRI" Mag. Reson. Med., 1995.*

Kalra S, Arnold D.L., Cashman N.R., Biological markers in the diagnosis and treatment of ALS, 1999, Journal of the Neurological Sciences 165:S27–S32.*

Bensimon G, Lacomblez L, Meinger V, A Controlled Trial of Riluzole in Amyotrophic Lateral Sclerosis, 1994, New England Journal of Medicine 330:585–591.*

Kalra Sanjay, Genge Angela, Cashman Neil, Antel Jack P., Arnold Douglas L., Monitoring Benefit to Upper Motor Neurons from Riluzole Therapy in ALS Using Proton Magnetics Resonance Spectroscopic Imaging, Mar. 1997, Neurology 48:129.*

* cited by examiner

Primary Examiner—Marvin M. Lateef
Assistant Examiner—Shawna J Shaw
(74) Attorney, Agent, or Firm—Swabey Ogilvy Renault; France Côté

(57) ABSTRACT

The present invention relates to a method to measure in vivo the effect of a drug on the function of the nerve cells of the brain of a patient suffering from a neurological disease, which comprises the steps of: a) measuring NAA signal intensity using MRS of the brain of the patient; b) subjecting the patient to a treatment with the drug to be tested and measuring NAA signal intensity using MRS of the brain of the patient; and c) comparing the spectra of steps a) and b) to determine whether the drug has an effect on the function of the nerve cells of the brain; whereby the increase in the NAA signal of step b) is indicative of a drug with a positive effect.

4 Claims, 2 Drawing Sheets

METHOD OF EVALUATING THE EFFICACY OF DRUG ON BRAIN NERVE CELLS

BACKGROUND OF THE INVENTION (a) Field of the Invention

The invention relates to a method of evaluating the efficacy of drugs on brain nerve cells based on the use of proton magnetic resonance spectroscopy.

(b) Description of Prior Art

Amyotrophic lateral sclerosis (ALS) is a progressive, usually sporadic form of motor neuron disease (MND) affecting both the upper motor neurons (UMNs) and the lower motor neurons (LMNs). The motor neurons are the postulated primary targets of the disease process. The relationship of MNDs involving solely the UMNs (primary lateral sclerosis (PLS)) or LMNs (progressive spinal muscular atrophy (PSMA)) with ALS remains to be established. Pure LMN syndromes may be present in hexosaminidase deficiency and immune-associated syndromes which, in some cases, may be amenable to specific therapies.

Magnetic resonance spectroscopy (MRS.) is similar to conventional magnetic resonance imaging (MRI), and is performed using basically the same equipment with relatively minor hardware and software modifications. However, whereas MRI provides anatomical information based on signals from water, MRS. Prides chemical information from metabolites That are present in tissues at much lower concentration than water.

Proton magnetic resonance spectroscopic imaging ($^1$H-MRS.) Prides the ability to noninvasively evaluate regional chemical pathology of human brain in vivo. Proton MR spectra of human brain reveal two signals of interest for this application: a signal from N-acetyl groups (mainly N-acetylaspartate) (NAA) and a signal from creatine (Cr). NAA is found exclusively in neurons and neuronal processes in the normal mature brain (Moffett J R, Namboodiri M A A, Cangro C B, Neale J H, 1991, *NeuroReport*, 2:131–134; simmons M L, Frondoza C G, Coyle J T, 1991, *Neuroscience*, 45:37–45) and, thus, can be used as a marker of neuronal integrity. Cr is present in all cells of the brain and can be used as an internal standard. The expression of NAA signal intensity relative to Cr (NAA/Cr) allows for easy comparison of NAA signal intensity (and, by implication, neuronal integrity) between different subjects.

$^1$H-MRS can be used to assess and monitor the evolution of neuronal or axonal damage in various conditions, including MS, stroke, human immunodeficiency virus-associated cognitive impairment and Alzheimer's disease.

A major problem in assessing drug efficacy in neurodegenerative disease is the lack of efficient clinical outcome measures. As a result of this, large multicenter trials are generally necessary. Such trials cost many millions of dollars, and may produce negative results, as did recent trial of ciliary neuronotropic factor and brain-derived neuronotropic factor. An efficient surrogate marker of efficacy would, therefore, be extremely valuable.

MRS has been used for a number of years now to assess neuronal and axonal loss based on the signal intensity of N-acetyl groups, which comes primarily from NAA in brain. The Applicants have used the signal to quantify the severity of disease and follow its progression based on decreases in NAA over time. Recently, we have reported the fact that decreases in NAA can spontaneously recover with time after certain brain injuries (multiple sclerosis relapses and some kinds of stroke). (De Stefano N, Matthews P M, Arnold D L, 1995, *Magn. Reson. Med.*, 34:721–727).

However, to date there exist no means to assess in vivo whether a drug has any positive effect on the brain function of a patient, such as restoring its NAA signal.

SUMMARY OF THE INVENTION

In accordance with the present invention, the Applicants have now discovered that abnormally low NAA levels can made to increase with effective drug therapy in patients with amyotrophic lateral sclerosis (ALS). This indicates that NAA can be used as a marker of improved neuronal function as well as a marker of neuronal loss. The use of MRS to measure increases in NAA as a marker of drug efficacy is novel and provides unexpected and unprecedented results.

In accordance with the present invention there is provided a method to measure in vivo the effect of a drug on the function of the brain of a patient suffering from a neurologic disease, which comprises the steps of:

a) obtaining $^1$H-MR spectra of the brain of the patient and measuring the signals from NAA;

b) subjecting the patient to a treatment with the drug to be tested and measuring the signals from NAA in the brain of the patient; and c) comparing the spectra of steps a) and b) to determine whether the drug has an effect on the function of nerves cells in the brain; whereby the increase in the NAA signal of step b) is indicative of a drug with a positive effect.

The term "neurologic diseases" when used herein is intended to mean, any neurologic diseases including strokes, multiple sclerosis, amyotrophic lateral sclerosis, epilepsy and neurodegenerative diseases such as Alzheimer's disease among others.

This invention can also be used to monitor drug improvement produced by treatment of other neurodegenerative diseases for which NAA decline has been observed with disease progression (such as Alzheimer's disease). Moreover, spontaneous improvement with time in NAA observed in certain types of cerebrovascular insults, and in acute exacerbations of multiple sclerosis (D L. Arnold et al., 1992, *Proc. Soc. Magn. Reson. Med.*, 1:643; N. De Stefano et al., 1995, *Neurology*, 45:1193–1198; N. De Stefano et al., 1995, *Magn. Reson. Med.*, 34:721–727) also indicate that drug therapies for these disorders may be tested in MRSI to assay for more complete or more rapid NAA recovery with novel drug therapies. This invention will help identify agents useful to human neurological therapeutics before the initiation of full scale clinical trials, and will help identify dosing regiments that may be most effective in such clinical trials.

DETAILED DESCRIPTION OF THE INVENTION

In accordance with the present invention, there is provided the use of proton MRS to monitor therapeutic efficacy on neuronal function based on increases in the signal from the neuronal marker, NAA. In accordance with the present invention, we have demonstrated the principle in the case of RILUZOLE™ (2-amino-6-trifluoromethoxy-benzothiazole) treatment for ALS. ALS is a neurodegenerative disease in which glutamate excitotoxicity is believed to play a pathogenetic role RILUZOLE™ (2-amino-6-trifluoromethoxy-benzothiazole), a glutamate release inhibitor antagonist, has been demonstrated in phase lll clinical trials to prolong the life of patients with ALS (Bensimon G. Lacomblez L, Meininger V, 1994, *N. Engl. J. Med.*, 330:585–591; Lacomblez L, Bensimon G. Leigh P N, Guillet P, Meininger V, 1996, *Lancet*, 347:1425–1431). We used proton MRS to monitor the signal intensity of NAA in the motor cortex of patients with ALS and succeeded in detecting an acute (within 3 weeks) increase in the signal from NAA after RILUZOLE™ (2-amino-6-trifluoromethoxy-benzothiazole) treatment (FIGS. 1A and 1B).

Figure 1A:
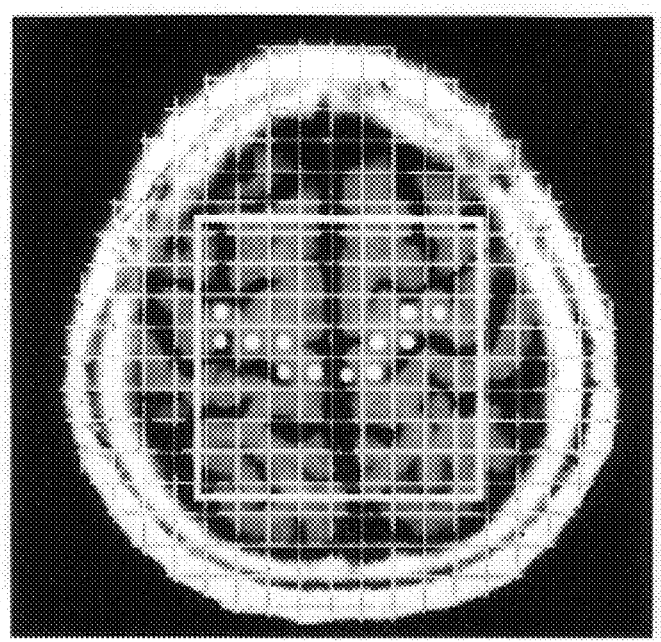
FIG. 1A illustrates an MRI with superimposed phase-encoding grid for MRSI in a patient with ALS with the voxels in the precentral gyrus of both hemispheres labeled with solid circles.
Figure 1B:
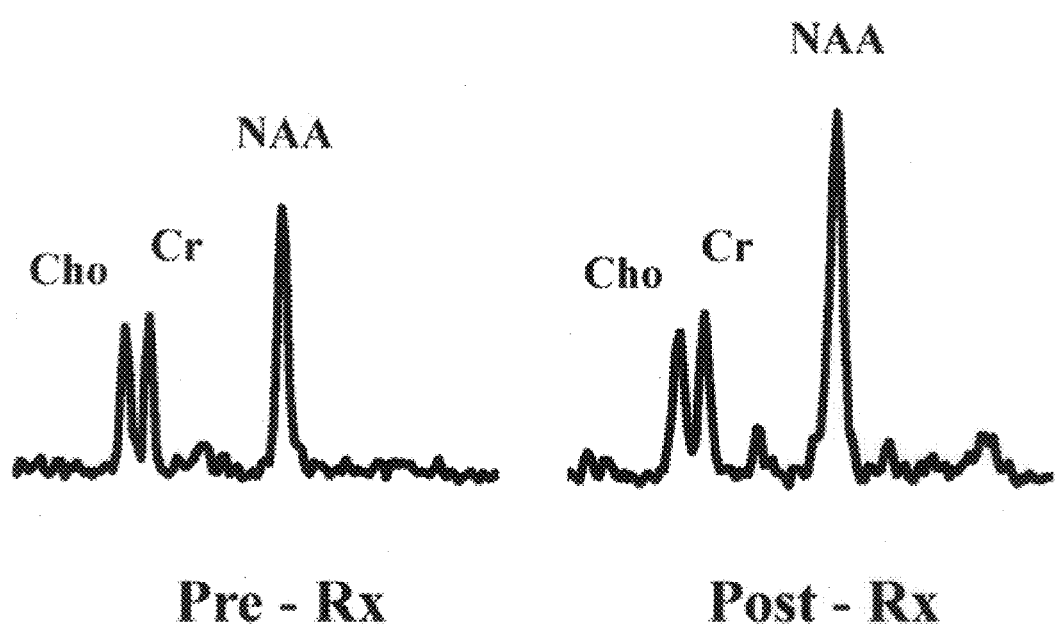
FIG. 1B illustrates the averaged MRI spectra from voxels in the precentral gyrus of a patient with ALS before and after and after 3 weeks of treatment with RILUZOLE™ (2-amino-6-trifluoromethoxy-benzothiazole)

FIGS. 1A and 1B illustrate an example based on a patient with ALS treated with RILUZOL™ (2-amino6-trifluoromethoxy-benzothiazole) showing an acute (3 weeks) increase in the signal from NAA in his motor cortex with respect to Cr. Inset shows a conventional MRI with the phase-encoding grid for spectroscopic imaging superimposed and the motor cortex outlined with a dashed line. Spectrum before treatment shows lower NAA than normal. Spectrum after treatment shows increased NAA suggesting improved neuronal function.

The demonstration of this phenomenon is valuable as it may provide a surrogate marker of response, as well as providing information on dosing and individual patient responsiveness to treatment.

In accordance with the method of the present invention, treatments may be tested to determine their effect on the function of brain. Such treatment includes any therapeutic agent, the action of which is directed at neurons, such as RILUZOLE™ (2-amino-6-trifluoromethoxy-benzothiazole), Gabapentin, zidovudine and sodium dichloroacetate.

This invention can also be used to monitor drug improvement produced by treatment of other eurodegenerative diseases for which NAA decline has been observed (such as Alzheimer's disease). Moreover, spontaneous improvement with time in NAA observed in certain types of cerebrovascular insults, and in acute exacerbations of multiple sclerosis (D L. Arnold et al., 1992, *Proc. Soc. Magn. Reson. Med.*, 1:643; N. De Stefano et al., 1995, *Neurology*, 45:1193–1198; N. De Stefano et al., 1995, *Magn. Reson. Med.*, 34:721–727) also indicate that drug therapies for these disorders may be tested by MRS to assay for more complete or more rapid NAA recovery with novel drug therapies. This invention will help identify agents useful to human neurological therapeutics before the initiation of full scale clinical trials, and will help identify dosing regiments that may be most effective in such clinical trials.

The present invention will be more readily understood by referring to the following examples which are given to illustrate the invention rather than to limit its scope.

EXAMPLE I

MRS methods of the present invention used for the detection of increased NAA in response to RILUZOLE™ (2-amino4-trifluoromethoxy-benzothiazole) treatment Nineteen patients with a diagnosis of definite or probable ALS, as per the El Escorial Criteria,[12] were recruited. Each patient underwent paired MRSI examinations. Eleven had their first scan just before commencing treatment and a second approximately three weeks after starting RILUZOLE™ (2-amino-6-trifluoromethoxy-benzothiazole) (50 mg bid); this group was designated ALS-R. Nine patients opting for no treatment had paired scans separated by approximately 3 weeks. Of the 11 treated patients 3 had had an additional scan approximately 3 weeks before starting treatment. Thus, closely paired MRSIs were obtained off medication in 12 subjects who formed a disease control group ALS-C.

Eleven had their first scan just before commencing treatment and a second approximately three weeks after starting Riluzole™ (50 mg bid); this group was designated ALS-R. Nine patients opting for no treatment had paired scans separated by approximately 3 weeks. Of the 11 treated patients 3 had had an additional scan approximately 3 weeks before starting treatment. Thus, closely paired MRSIs were obtained off medication in 12 subjects who formed a disease control group ALS-C.

Magnetic Resonance Spectroscopic Imaging

Brain proton spectroscopy was performed using a Philips Gyroscan ACS3 operating at 1.5 Tesla (Philips Medical System, Best, The Netherlands). After axial and sagittal scout images and sagittal T1-weighted images were obtained, axial T1-weighted images were acquired with an angulation determined from sagittal T1-weighted images such that the transverse plane was perpendicular to the rostral-caudal axis of the precentral gyrus. These transverse scans were used to select a volume of interest (VOI) centered on the central sulcus, high in the cranium comprised of predominantly cortical brain (FIG. 1A). Craniocaudal (CC) thickness was 20 mm. Anteroposterior (AP) and left-right (LR) dimensions were adjusted for each patient depending on the skull size and shape to maximize size without including skull. MRSI was performed using a 90°–180°–180° (PRESS) sequence (TR=1750, TE=272, 250×250 mm FOV, 32×32 phase-encoding steps) with prior suppression of water by selective excitation. One patient had all his scans performed with TR=1500. The ROI was repositioned in the identical location in follow up scans of each patient.

$^1$H-MRS. Data Post-processing

Post-processing of data, included a mild Gaussian filter and an inverse two-dimensional Fourier transform of both the water-suppressed and -unsuppressed $^1$H-MRS. This was accomplished with XUNSPEC1 software (Philips Medical Systems Best, The Netherlands) running on a Sun SPARC™ station.

The residual water signal was removed using the HSVD (Hankel Singular-Value Decomposition) algorithm which models the time-domain $^1$H-MRS data in each voxel with exponentially damped sinusoids. Peaks used to model the water signal were then subtracted from the original data. This algorithm is fully automatic and requires no prior knowledge or operator intervention.

$^1$H-MRS. Data Reduction

Automated calculation of metabolite peak areas was performed on operator-selected voxels within the motor cortex. Peaks were digitally integrated to yield areas. These values were normalized by dividing them by that of Cr.

Statistical Methods

The NAA/Cr of the primary motor cortex was determined by averaging the NAA/Cr intensities of voxels located in the precentral gyrus of both hemispheres (FIGS. 1A and 1B). The difference in motor cortex NAA/Cr between two scans (ΔNAA/Cr) obtained approximately 3 weeks apart was determined for each ALS patient in the treated (ALS-R) and control (ALS-C) groups. ΔNAA/Cr was compared between the treated and control groups using a two-sample two-sided Student's t-test. In addition, a two-sided paired Student's t-test was used to evaluate the significance of αNAA/Cr within each group.

Results

Nineteen patients with ALS (7 females, 12 males, average age 64±11 years, baseline NAA/Cr 2.19±0.21) were studied. Demographic characteristics, motor cortex NAA/Cr observed in paired scans, and the change in NAA/Cr between paired scans are presented in Table 1. There was no statistically significant difference in sex, age, disease duration, baseline NAA/Cr, or frequency of upper motor neuron or bulbar involvement between the ALS-R and ALS-C groups.

Figure 2:
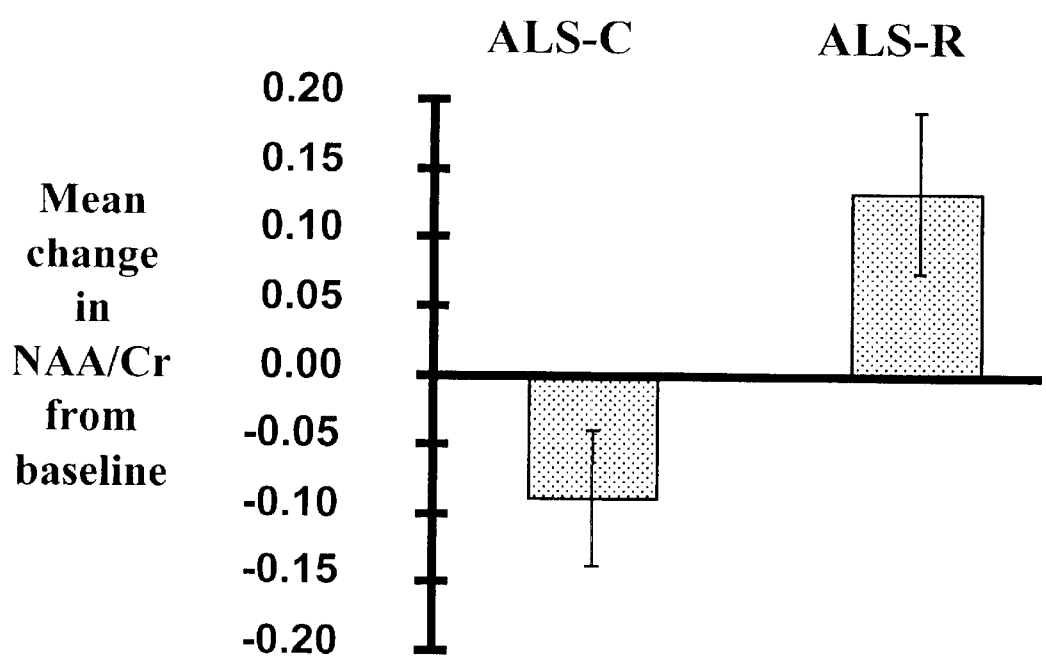
FIG. 2 illustrates a bar graph showing the mean change in NAA/Cr in 11 patients treated with RILUZOLE™ (2-amino-6-trifluoromethoxy-benzothiazole) (ALS-R) compared to 12 patients who received no treatment (ALS-C).

Approximately 24±8 days after initiating RILUZOLE™ (2-amino6-trifluoromethoxy-benzothiazole) therapy in 11 patients (ALS-R) the average NAA/Cr for the group increased from 2.14±0.26 to 2.27±0.24 (mean±SD, p=0.044). In 12 patients not receiving medication (ALS-C) the average NAA/Cr for the group decreased from 2.17±0.20 to 2.08±0.20 (mean±SD, p=0.099) over a period of 21±6 days. Thus, the change in NAA/Cr for the treated group with respect to the untreated group was an increase of 0.22±0.095 (mean±SE, p=0.008) (FIG. 2). Note the rise in NAA/Cr after approximately 3 weeks of treatment with RILUZOLE™ (2-amino-6-trifluoromethoxy-benzothiazole) versus the decrease in the untreated group. Standard error bars are shown.

Absolute motor cortex Cr signal intensities did not change between paired exams in either the treated (p=0.89) or untreated groups (p=0.97).

In patients treated with RILUZOLE™ (2-amino-6-trifluoromethoxy-benzothiazole), there was no significant correlation between ΔNAA/Cr and age, pretreatment NAA/Cr, and duration of treatment or disease. There was no difference in ΔNAA/Cr with RILUZOLE™ (2-amino-6-trifluoromethoxy-benzothiazole) treatment between males or females, patients with definite or probable UMN signs, and patients with or without bulbar features.

Only one patient described symptomatic and functional changes during the few weeks of therapy between two scans: patient#11 described improved strength and reduced disability (less difficulty raising arms and climbing stairs) after 35 days of RILUZOLE™ (2-amino-6-trifluoromethoxy-benzothiazole) therapy. Deltoid and iliopsoas MRC grades improved bilaterally from 4 to 4+.

Several patients agreed to longer term follow up studies. In patient #2, NAA/Cr increased from 2.53 to 2.64 after 35 days of RILUZOLE™ (2-amino-6-trifluoromethoxy-benzothiazole) therapy; three months later it increased further to 2.74, at which time he reported increased strength and fewer cramps. In patient #3, NAA/Cr increased from 2.00 to 2.44 after 18 days of RILUZOLE™ (2-amino-6-trifluoromethoxy-benzothiazole) therapy; three months later it had dropped to 1.46 associated with significant clinical deterioration including increased dysarthria and weakness. In patient #5, NAA/Cr increased from 2.24 to 2.31 after 21 days of therapy and further to 2.42 one year later; weakness, with predominantly LMN features, slowly progressed. Patient #17 was never treated: NAA/Cr decreased from 2.51 to 2.42 after 21 days and further to 2.11 4 months later; his symptoms progressed slowly.

Discussion

Using proton MRSI to measure the neuronal marker NAA, we have demonstrated a rise in the relative intensity of NAA in the primary motor cortex of patients with ALS within 3 weeks of starting RILUZOLE™ (2-amino-6-trifluoromethoxy-benzothiazole) therapy. Longer-term follow-up scans revealed some correlation between the changes in NAA/Cr and the clinical status of several patients.

Low NAA/Cr in vivo has been observed in numerous neurological disorders associated with neuronal loss or damage, and appears to result from either: (i) a decrease in the intracellular volume of neurons per unit volume of brain (due to either neuronal loss or atrophy), or (ii) a decrease in the concentration of NAA within neurons due to metabolic dysfunction. [13-19]

Recovery of NAA has been observed in a variety of situations associated with recovery of neuronal integrity; for example, in patients recovering from acute demyelinating lesions or strokes, after successful surgery for temporal lobe epilepsy or carotid occlusive disease, and after instituting anti-retroviral therapy in AIDS.

As discussed by De Stefano, reversible changes in NAA/Cr most likely result from either an increase in the volume of NAA-containing neurons (including dendrites and axons) per unit volume of brain or an increase in the concentration of NAA within neurons. Since CNS neurons have a limited capacity to regenerate, increases in relative neuronal volume would have to result from increases in the volume of existing neurons. Dendritic atrophy has been reported in ALS. Reversal of neuronal atrophy, for example, due to dendritic sprouting, may be contributing to the observed increases in NAA/Cr in response to RILUZOLE™ (2-amino-6-trifluoromethoxy-benzothiazole) therapy. Increases in the concentration of NM within neurons may also be contributing to the observed increases in NM after RILUZOLE™ (2-amino-6-trifluoromethoxy-benzothiazole) therapy. Mitochondria can be injured by glutamate-mediated excitotoxicity. NAA is synthesized in the mitochondria of neurons, and inhibition of the mitochondrial respiratory chain is known to result in diminished NAA production, Therefore, reduced glutamate-mediated excitotoxic mitochondrial damage could lead to increases in the concentration of NM within neurons after instituting RILUZOLE™ (2-amino-6-trifluoromethoxy-benzothiazole) therapy.

It is unlikely that the observed changes in NAA/Cr represent a methodological artifact. There is no theoretical reason to expect a change in the relaxation properties of NAA with respect to Cr in the patients who were treated vs. Those who were untreated. Possible effects of differences in the content of white and grey matter would similarly not be expected to systematically affect the treated group. Finally, in vitro studies using high performance liquid chromatography to measure NAA in cultured neuronal cells also show reversible decreases in NAA after metabolic stress.

Conclusions

Assessment of corticomotoneuron integrity and function is difficult in ALS. Commonly used clinical outcome measures reflect both upper and lower motor neuron dysfunction. This study demonstrates that MRSI can be used to monitor specifically an improvement in UMN integrity, which is otherwise difficult to detect and quantify. Changes in NM could thus provide an important and useful surrogate marker for therapeutic response. Although the augmentation of NAA/Cr in motor cortex does not necessarily imply that neuronal survival will be extended with corresponding clinical benefit, these clinical benefits have already been demonstrated for RILUZOLE™ (2-amino-trifluoromethoxy-benzothiazole) therapy of ALS. Thus, we believe that the potential for NAA/Cr to become a valid surrogate for therapeutic response in ALS is promising.

TABLE 1

Patient Characteristics and Data

| | Age | Sex | Disease Duration (months) | El Escorial designation | Bulbar features¶ | UMN features¶ | NAA/Cr MRSI #1£ | NAA/Cr MRSI #2£ | ΔNAA/Cr |
|---|---|---|---|---|---|---|---|---|---|
| Patient Treated (ALS-R) n = 11 | | | | | | | | | |
| 1 | 74 | m | 24 | definite | Yes | Yes | 2.519 | 2.508 | −0.011 |
| 2 | 35 | m | 12 | definite | Yes | Yes | 2.532 | 2.643 | 0.111 |
| 3 | 56 | m | 2 | definite | Yes | Yes | 2.004 | 2.442 | 0.438 |
| 4 | 73 | f | 24 | probable | No | Probable | 2.121 | 2.416 | 0.295 |
| 5 | 67 | f | 36 | probable | No | probable | 2.305 | 2.423 | 0.118 |
| 6 | 78 | f | 24 | definite | No | probable | 2.057 | 2.291 | 0.234 |
| 7 | 55 | f | 24 | probable | No | probable | 1.911 | 1.890 | −0.021 |
| 8 | 68 | m | 32 | probable | No | probable | 2.334 | 2.083 | −0.251 |
| 9 | 61 | f | 12 | probable, familial | Yes | probable | 2.025 | 2.247 | 0.222 |
| 10 | 75 | m | 36 | probable | Yes | Yes | 1.679 | 1.969 | 0.290 |
| 11 | 57 | f | 180 | probable, familial | No | Yes | 2.019 | 2.053 | 0.034 |
| Mean | 64 | | 37 | | | | 2.14 | 2.27 | 0.13 |
| SD | 13 | | 49 | | | | 0.26 | 0.24 | 0.19 |
| Patient Treated (ALS-C) n = 12 | | | | | | | | | |
| 5 | 67 | f | 36 | probable | No | probable | 2.235 | 2.305 | 0.070 |
| 6 | 78 | f | 24 | definite | No | probable | 2.009 | 2.057 | 0.048 |
| 7 | 55 | f | 24 | probable | No | probable | 2.002 | 1.911 | −0.091 |
| 10 | 75 | m | 36 | probable | Yes | Yes | 2.284 | 1.907 | −0.377 |
| 12 | 77 | m | 12 | definite | No | Yes | 2.320 | 2.141 | 0.179 |
| 13 | 71 | f | 36 | probable | No | probable | 1.901 | 2.003 | 0.102 |
| 14 | 65 | m | 120 | definite | Yes | Yes | 2.033 | 1.830 | −0.203 |
| 15 | 79 | m | 36 | definite | Yes | Yes | 2.148 | 1.826 | −0.322 |
| 16 | 62 | m | 10 | definfte | Yes | No | 1.915 | 2.110 | 0.195 |
| 17 | 50 | m | 72 | definite | Yes | Yes | 2.515 | 2.422 | −0.093 |
| 18 | 63 | m | 144 | probable | Yes | Yes | 2.157 | 2.039 | −0.118 |
| 19 | 51 | m | 6 | probable | Yes | Yes | 2.459 | 2.358 | −0.101 |
| Mean | 66 | | 46 | | | | 2.17 | 2.08 | −0.09 |
| SD | 10 | | 44 | | | | 020 | 0.20 | 0.17 |

UMN = Upper Motor Neuron
¶Criteria for UMN and bulbar involvement per E1 Escorial Criteria
£NAA/Cr of motor cortex
ΔNAA/Cr = Change in NAA/Cr between MRSI scan #1 and #2

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method to measure in vivo the effect of a drug on the function of the nerve cells of the brain of a patient suffering from a neurological disease, which comprises the steps of:
   a) measuring N-acetylaspartate (NAA) signal intensity using magnetic resonance spectroscopy (MRS) of the brain of the patient;
   b) subjecting the patient to a treatment with the drug to be tested and measuring NAA signal intensity using MRS of the brain of the patient; and
   c) comparing the spectra of steps a) and b) to determine whether the drug has an effect on the function of the nerve cells of the brain; whereby the increase in the NAA signal of step b) is indicative of a drug with a positive effect.

2. The method of claim 1, wherein the drug to be evaluated is selected from the group consisting of RILUZOLE™ (2-amino-6-trifluoromethoxy-benzothiazole), Gabapentin, zidovudine and sodium dichloroacetate.

3. The method of claim 1, wherein the neurologic disease is selected from the group consisting of strokes, multiple sclerosis, amyotrophic lateral sclerosis, epilepsy and neurodegenerative diseases.

4. The method of claim 3, wherein the neurodegenerative disease is Alzheimer's disease.

* * * * *